United States Patent [19]

Dagan

[11] Patent Number: 5,292,031

[45] Date of Patent: Mar. 8, 1994

[54] CONTAINER FOR CONTACT LENS SOLUTION

[76] Inventor: Baruch Dagan, 296 Torresdale Ave., Unit #4, Willowdale, Ontario, Canada, M2R 3N3

[21] Appl. No.: 929,400

[22] Filed: Aug. 14, 1992

[51] Int. Cl.⁵ ............................................. B65D 35/22
[52] U.S. Cl. ...................................... 222/1; 222/105; 222/94; 222/181
[58] Field of Search ............... 222/92, 94, 105, 181, 222/1; 134/901; 206/5.1

[56] References Cited

U.S. PATENT DOCUMENTS

| | | | |
|---|---|---|---|
| 3,221,939 | 1/1962 | Brown | 222/94 |
| 3,473,886 | 10/1969 | Leeds | 206/5.1 |
| 4,085,867 | 4/1978 | Heller | 222/181 |
| 4,368,729 | 1/1983 | Dossin | 128/214 |
| 5,016,779 | 5/1991 | Williamson | 222/105 |
| 5,083,678 | 1/1992 | Waring | 222/105 |
| 5,105,993 | 4/1992 | La Haye et al. | 222/189 |
| 5,186,359 | 2/1993 | Brown et al. | 222/94 |
| 5,186,559 | 2/1993 | Fu | 222/94 |

Primary Examiner—Andres Kashnikow
Assistant Examiner—Lesley D. Morris
Attorney, Agent, or Firm—Adrian Zahl

[57] ABSTRACT

A dispenser for contact lens solutions is provided, comprising a support structure and at least one flexible and collapsible container supported therefrom. An outlet extends from the bottom of the container, the outlet having a valve adapted to allow the outflow of solution while preventing backflow or the entry of air into the container. The container may be provided with multiple compartments for separate solutions, or multiple containers may be provided. There is further provided a method for storing and dispensing contact lens solution with the dispenser.

8 Claims, 5 Drawing Sheets

CONTAINER FOR CONTACT LENS SOLUTION

FIELD OF INVENTION

The present invention relates generally to a method of preparing a contact lens for wearing and more particularly to a flexible, disposable and collapsible multidose container for storing and dispensing of solutions in the use with contact lenses.

BACKGROUND OF THE INVENTION

Within the prior art there exists a disposable package or container for storing and discharging a small unit of chemical solutions. U.S. Pat. No. 3,221,939 by Brown describes such a device used for storing and dispensing small quantities of liquids. Another example of a container for storing and discharging a solution is found in U.S. Pat. No. 5,105,993 wherein a disposable container for dispensing sterile liquid medication is disclosed. However, to maintain the sterility of the solutions, the container of the above prior arts are made sterile. The containers are sterilized with ethylene oxide which increases the cost of packaging of an ophthalmic solution significantly.

Repeated use of the ophthalmic solution from the container of the prior art increases the probability that microbial contaminants will be introduced into the solution. Thus, serious infections can be transferred from person to person in this way. To prevent this, antimicrobial preservatives are included into the solutions with the exception of those packaged for one time use. However, an increasing number of ophthalmologists prefer to use a non-preserved solution because patients have shown an allergic reaction to the commonly used preservatives.

Nowhere within the prior art is there found a collapsible and disposable airless package for storing and dispensing solutions in the use with contact lenses.

It is therefore an object of this invention to provide a multidose flexible container, for storing and dispensing contact lens solution, which does not require air venting to function; the container collapses while the solution is being drained.

It is a further object of this invention to provide a multidose disposable container that is capable to reduce waste volume, as opposed to conventional rigid containers, for storing and dispensing solutions in the use with contact lenses.

It is a further object of this invention to provide a flexible container, for storing and dispensing solutions in the use with contact lenses, which may not require the use of preservatives.

Further and other objects of the invention will become apparent to the man skilled in the art when considering the following summary of the invention and the more detail description of the preferred embodiments illustrated herein.

SUMMARY OF THE INVENTION

According to one aspect of the present invention there is provided a method of preparing a contact lens for wearing by the user (for example cleaning, disinfecting, neutralization, rinsing or the like) and the preparation of the contact lens being accomplished by a solution (such as cleaning, disinfecting, neutralization, rinsing or the like) contained within at least one flexible and collapsible container, upon dispensing, having two ends and having disposed at one end mounting means and having disposed proximate the other end interruptive outlet means, the outlet means being accessible to the user wearing the contact lens; said flexible and collapsible container, upon dispensing, contains a sterilized preparation of solution, said method comprises:

(a) supporting the flexible and collapsible, upon dispensing, container from the mounting means so as to be accessible to the user;
(b) accessing the interruptive outlet means by the user and applying the preparation to the contact lens;
(c) interrupting the flow of the preparation to the contact lens by the user; and
(d) where multiple preparations are used, repeating steps (b) and (c) as required for each preparation being used.

In a preferred embodiment the flexible and collapsible container, upon dispensing, may further comprise at least as many separate compartments accessible by the user as the number of fluids being used; for example where a cleaning solution and a neutralizing solution are used, the flexible and collapsible container, upon dispensing, may be formed with two separate compartments, each compartment preferably includes its own interruptive outlet means accessible by the user. This is preferred so as to prevent back flow or mixing of solution with another should one interruptive outlet means be provided.

According to yet another aspect of the present invention there is provided an apparatus for preparing a contact lens for wearing by a user comprising a flexible and collapsible container, upon dispensing, containing a cleaning, disinfecting, rinsing, or neutralizing solution, support means for supporting said container and interruptive outlet means for controlling the flow of said solution from said container.

According to yet another aspect of the present invention there is provided an apparatus for preparing a contact lens for wearing by a user, comprising at least two flexible and collapsible containers wherein one container holds disinfecting solution and the other holds a neutralizing solution, support means for supporting at least two flexible containers, interruptive outlet means for dispensing the solution out of each container, base means located proximate said interruptive outlet means, said base means for supporting contact lenses proximate said flexible tube means for cleaning, disinfecting, neutralizing, rinsing or the like.

In a preferred embodiment of any of the above apparatuses or methods for dispensing at least one sterile contact lens solution, the interruptive outlet means is always pointing substantially downwards such that no air can enter into the flexible and collapsible container upon dispensing.

BRIEF DESCRIPTION OF THE DRAWINGS

The invention will now be illustrated with respect to the following drawings illustrating embodiments of the invention in which.

DETAILED DESCRIPTION OF PREFERRED EMBODIMENTS OF THE INVENTION

Figure 1:
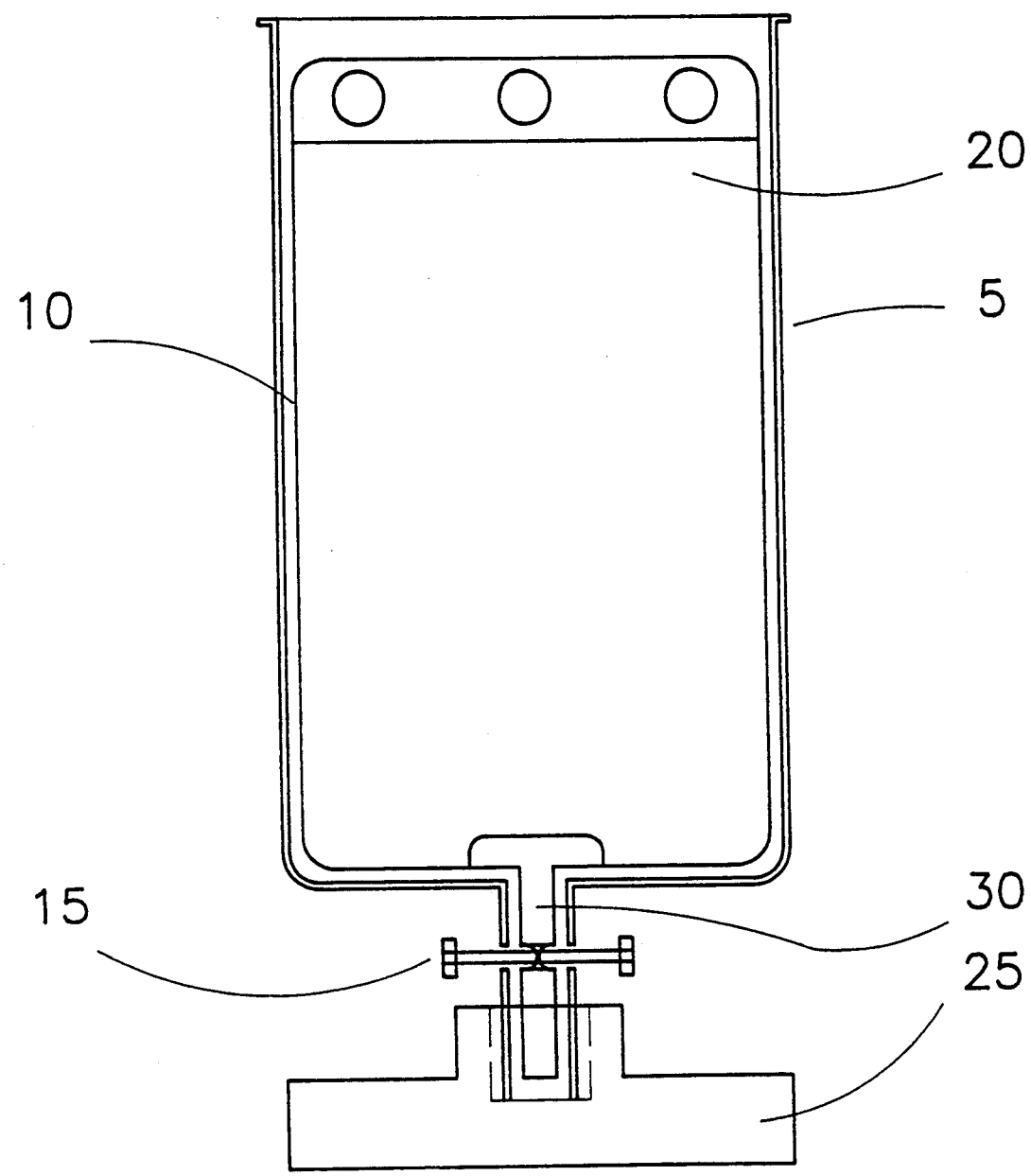
FIG. 1 is a front view of the container embodying the present invention.

Referring now to FIG. 1, there is illustrated a semi-rigid container holder generally designated at 5 which contains a flexible container 10 or the like wherein the said container 10 holds a fluid 20 for cleaning or disinfecting a contact lens. Said fluid 20 is prevented from flowing out of flexible container 10 by pinch valve 15. The semi-rigid container 5 is supported by base 25 when not in use. When the user wants to clean and/or disinfect the contact lens, the user will remove the semi-rigid container 5 which contains the flexible container 10 and apply force on the pinch valve 15 which will allow fluid 20 to be dispensed from the flexible container 10 via flexible tube 30. Upon completing the act of dispensing the fluid 20, the user will replace the semi-rigid container 5 on the base 25 for storage until next use.

Figure 2:
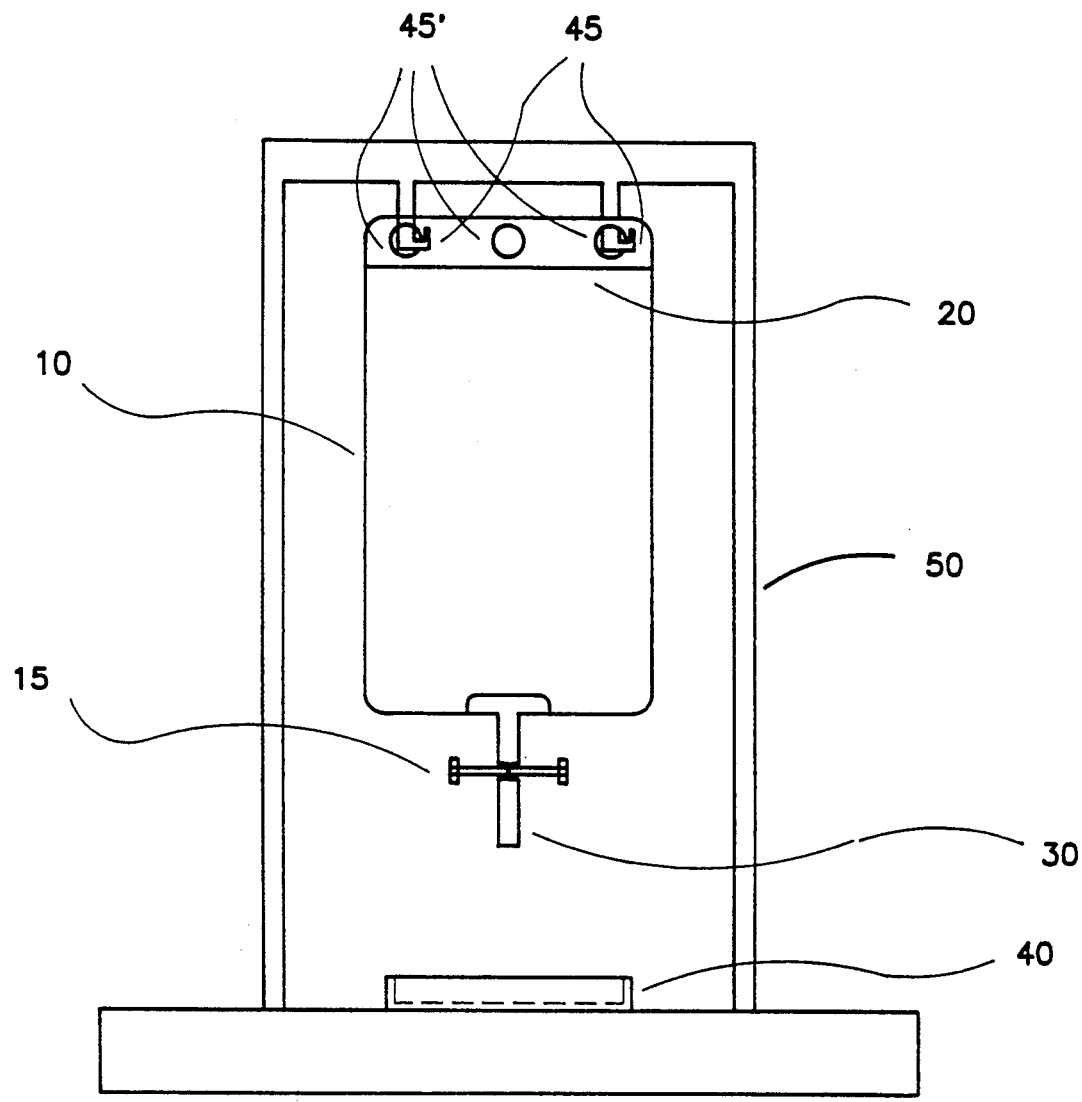
FIG. 2 is a view of the type of FIG. 1 illustrating a single frame container.

Referring now to FIG. 2, there is provided another preferred embodiment of the present invention. The flexible container 10 holding said fluid 20 is supported by a frame 50 containing two hooks 45 which are inserted through apertures 45' on said flexible container 10. The user can place said contact lenses on the contact lens holder 40 and proceed to squeeze the pinch valve 15 in order to dispense the fluid 20 from the flexible container 10.

Figure 3:
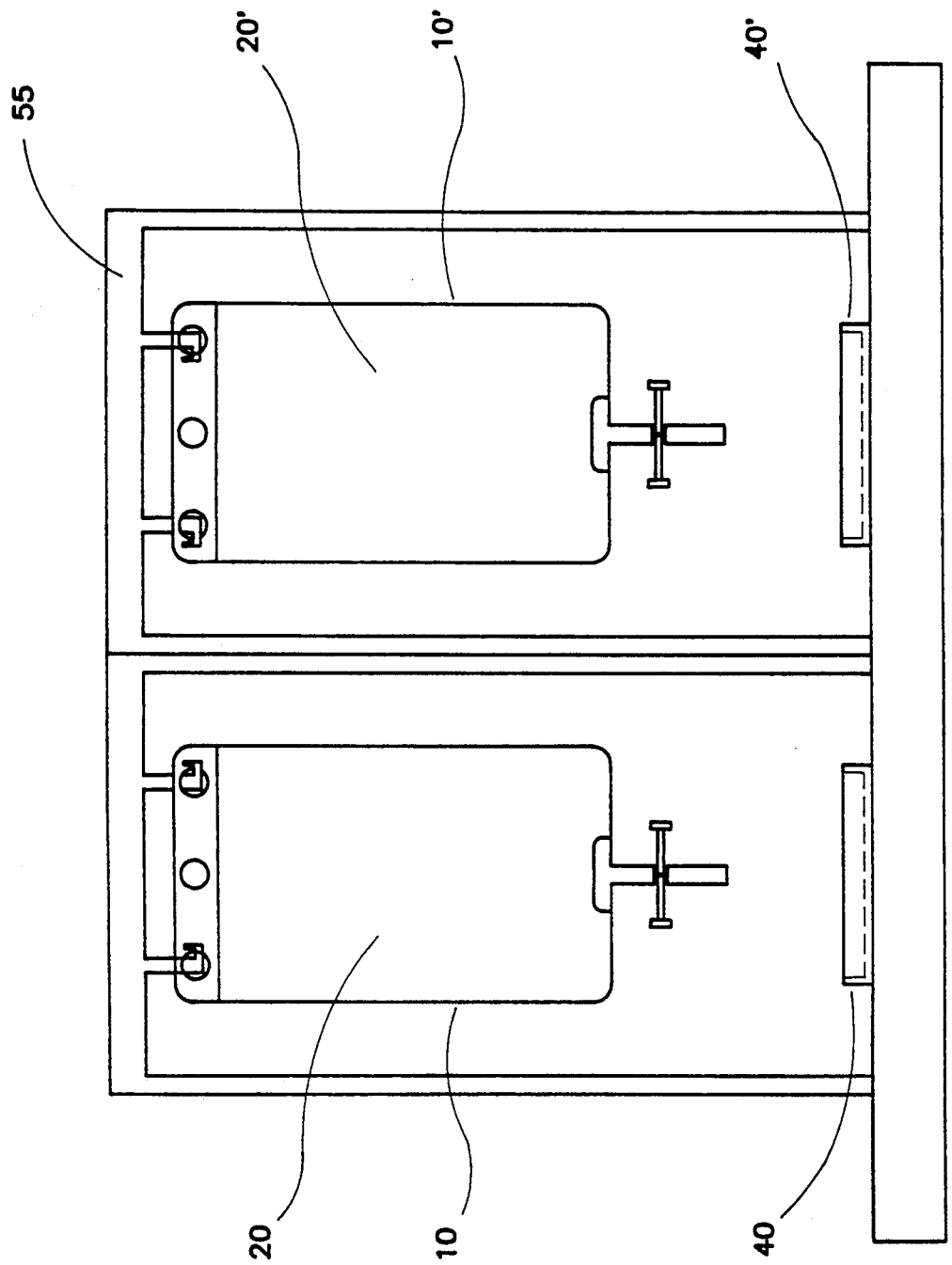
FIG. 3 is a front view of multiple frame container.

In FIG. 3, there is shown a frame support 55 which is capable of holding at least two flexible containers 10 and 10' where one container 10 contains a disinfecting fluid 20 and said container 10' contains a neutralizing fluid 20' such that when the user wants to disinfect and rinse the contact lenses, the user will first proceed to the contact lens holder 40 located below the flexible container 10 to disinfect the contact lenses and after disinfect of said lenses will move said contact lenses to the contact lens holder 40' located below the bag 10' to neutralize the lenses. This will reduce confusion of the user when disinfecting and neutralizing contact lenses.

Figure 4:
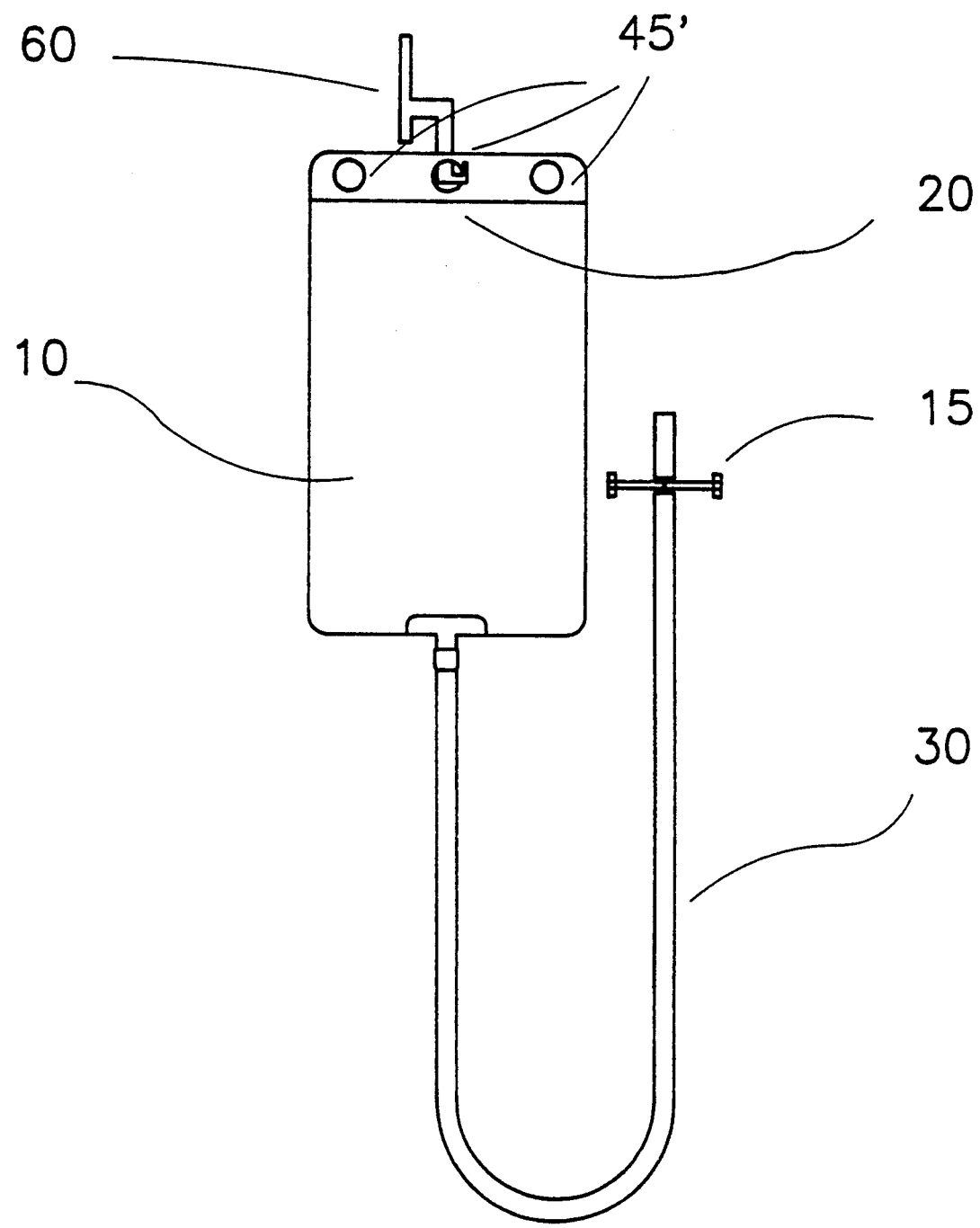
FIG. 4 is a front view of the container supported on a wall.

Referring now to FIG. 4 there is provide another preferred embodiment of the invention where said flexible container 10 containing a fluid 20 is supported on a wall via a support clip 60 which is held through one of the holes 45' located on the upper end of the flexible container 10. The flexible tube 30 is longer in this case to provide a greater degree of freedom when cleansing and/or rinsing the contact lenses. In this case the user would hold the flexible tube 30 and squeeze the pinch valve 15 in order to dispense the fluid 20 over the contact lenses. There can be provided a series of containers along a wall where each container would hold a cleansing fluid and/or a rinsing fluid.

Figure 5:
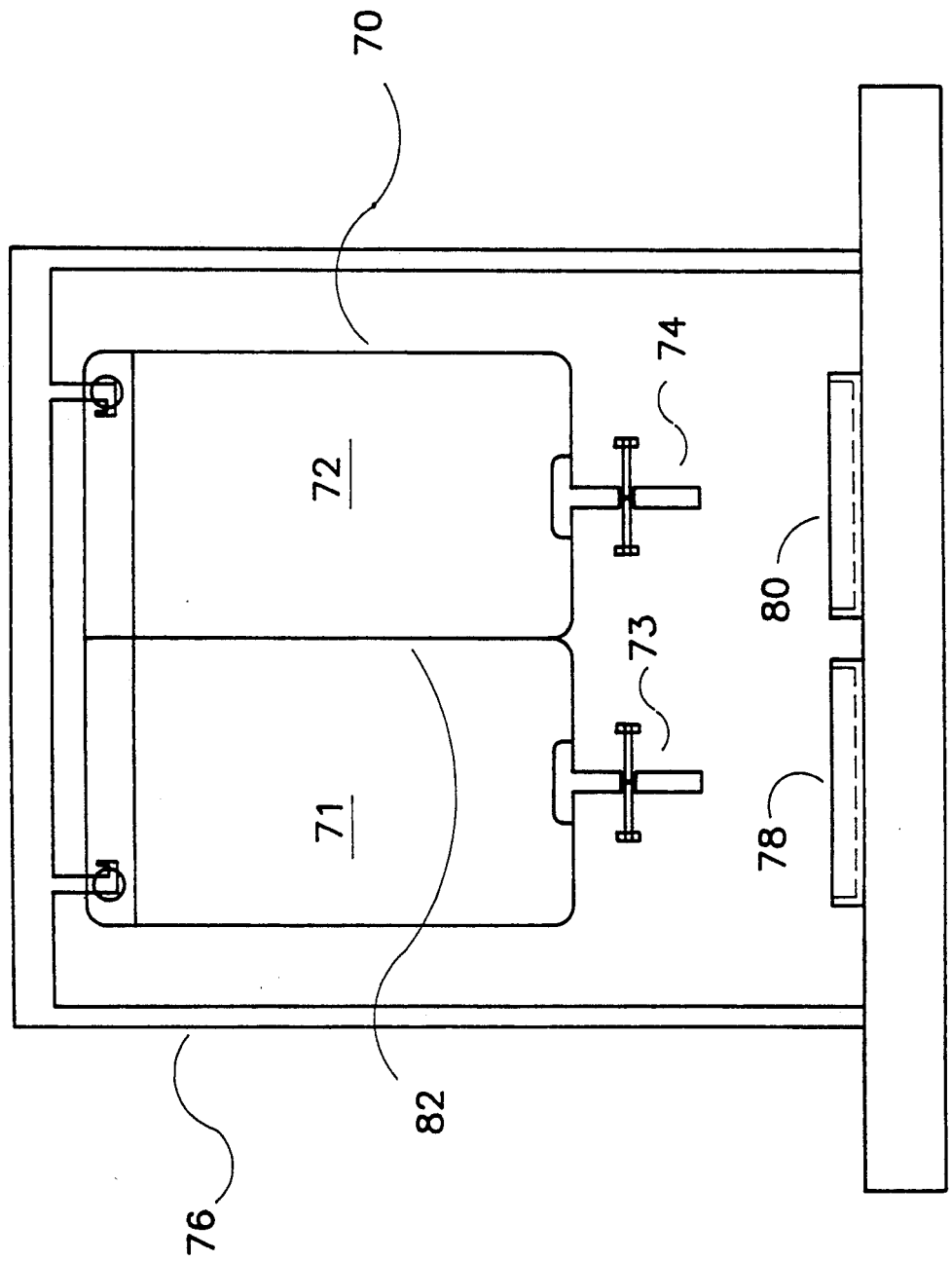
FIG. 5 is a front view of the container with plural compartments.

A further embodiment of the invention is shown in FIG. 5, wherein the flexible container 70 is comprised of two compartments 71 and 72 adapted to hold separate solutions. It will be apparent that the container may be divided into any number of separate compartments. Each compartment is provided with its own valve 73, 74. The container is suspended from a support 76, and each valve may be positioned over a separate contact lens holder 78, 80. The compartments 71, 72 are divided from each other by a divider 82. It will be apparent that other means may be employed of separating the compartments from each other, provided that the separate compartments do not leak into each other.

As will be apparent to those skilled in the art, various modifications and adaptations of the invention described above may be made without departing from the scope or spirit of the invention; the limitation of the scope of the embodiment of the invention are to be construed in accordance with the accompanying claims and not in a limiting sense.

The embodiments of the invention in which an exclusive property or privilege is claimed are as follows:

1. A dispenser for contact lens solution, comprising a support, at least two flexible and collapsible containers suspended from said support, and a valve extending from the bottom of said containers and adapted to selectively allow the outflow of solution from said containers, while substantially preventing backflow or the entry of air therein, said valve comprising a generally downwardly-pointing flexible tube extending from the bottom of said containers and communicating with the interior thereof and a pinch valve adapted to pinch said tube to selectively interrupt the flow of solution from said containers.

2. A dispenser as claimed in claim 1 wherein there is further provided a contact lens holder for holding at least one contact lens, said holder being positionable within said support under one of said containers.

3. A method for storing contact lens solution and dispensing said solution into a contact lens holder, comprising the steps of:
   a) storing sterilized contact lens solution within a flexible and collapsible container suspended from a support, said container having a valve extending from the bottom thereof and adapted to selectively allow the outflow of solution from said container, while substantially preventing backflow or the entry of air therein;
   b) actuating said valve to dispense said solution into said holder.

4. A method as claimed in claim 3, wherein at least two of said containers are provided, each container being suspended from said support and being provided with said valve means.

5. A method as claimed in claim 3 wherein there is further provided a contact lens holder for holding at least one contact lens, said holder being positionable within said support under said container.

6. A method as claimed in claim 3 wherein said container includes therein two or more compartments, each of said compartments adapted to contain a separate solution and each having a valve extending therefrom.

7. A method as claimed in claim 3 wherein said valve comprises a generally downwardly-pointing flexible tube extending from the bottom of said container and communicating with the interior thereof and a pinch valve adapted to pinch said tube to selectively interrupt the flow of solution from said container.

8. A dispenser for contact lens solution, comprising a support and a flexible and collapsible container suspended from said support, said container comprising two or more compartments each for the containment of a solution and each compartment having a valve extending from the bottom thereof adapted to selectively allow the outflow of solution therefrom, while substantially preventing backflow or the entry of air therein, said valve comprising a generally downwardly-pointing flexible tube and a pinch valve adapted to pinch the tube to selectively interrupt the flow of solution from the compartment.

* * * * *